(12) United States Patent
Rousseau et al.

(10) Patent No.: US 6,255,101 B1
(45) Date of Patent: Jul. 3, 2001

(54) SEAL FOR REAGENT FLASK USABLE BY A BLOOD ANALYZER

(75) Inventors: Alain Rousseau, Paris; Jean-François Gelin, Creteil, both of (FR)

(73) Assignee: Diagnostica Stago (FR)

( * ) Notice: Subject to any disclaimer, the term of this patent is extended or adjusted under 35 U.S.C. 154(b) by 0 days.

(21) Appl. No.: 09/341,953

(22) PCT Filed: Jan. 15, 1998

(86) PCT No.: PCT/FR97/00094

§ 371 Date: Jul. 21, 1999

§ 102(e) Date: Jul. 21, 1999

(87) PCT Pub. No.: WO98/32672

PCT Pub. Date: Jul. 30, 1998

(30) Foreign Application Priority Data

Jan. 24, 1997 (FR) .................................................. 97 00916

(51) Int. Cl.[7] .................................................. C12M 1/34
(52) U.S. Cl. .................................... 435/288.1; 435/304.1; 435/304.3; 215/247; 215/266; 215/312; 215/320; 215/341; 215/329; 220/367.1

(58) Field of Search ............................... 435/288.1, 304.1, 435/304.3; 215/200, 247, 307, 266, 312, 320, 355, 341, 329; 220/367.1, 373

(56) References Cited

U.S. PATENT DOCUMENTS 5,334,178 * 8/1994 Haber et al. .
5,455,180 * 10/1995 Reid .................................. 435/288.1

FOREIGN PATENT DOCUMENTS

| 1 300 463 | * | 7/1969 | (DE) . |
| 0 560 390 A1 | * | 9/1993 | (EP) . |
| 1 267 855 | * | 12/1961 | (FR) . |
| 2 188 565 | * | 1/1974 | (FR) . |
| 804 824 | * | 11/1958 | (GB) . |

* cited by examiner

Primary Examiner—David A. Redding
(74) Attorney, Agent, or Firm—William A. Drucker

(57) ABSTRACT

The invention concerns a seal for closing the neck of a flask. The seal comprises a stopper with a central coaxial channel for passage of an injection and/or sampling needle, this channel being sealed by at least one ball with a diameter slightly greater than that of the channel. This seal is suitable for a reagent flask used by a blood analyzer.

9 Claims, 2 Drawing Sheets

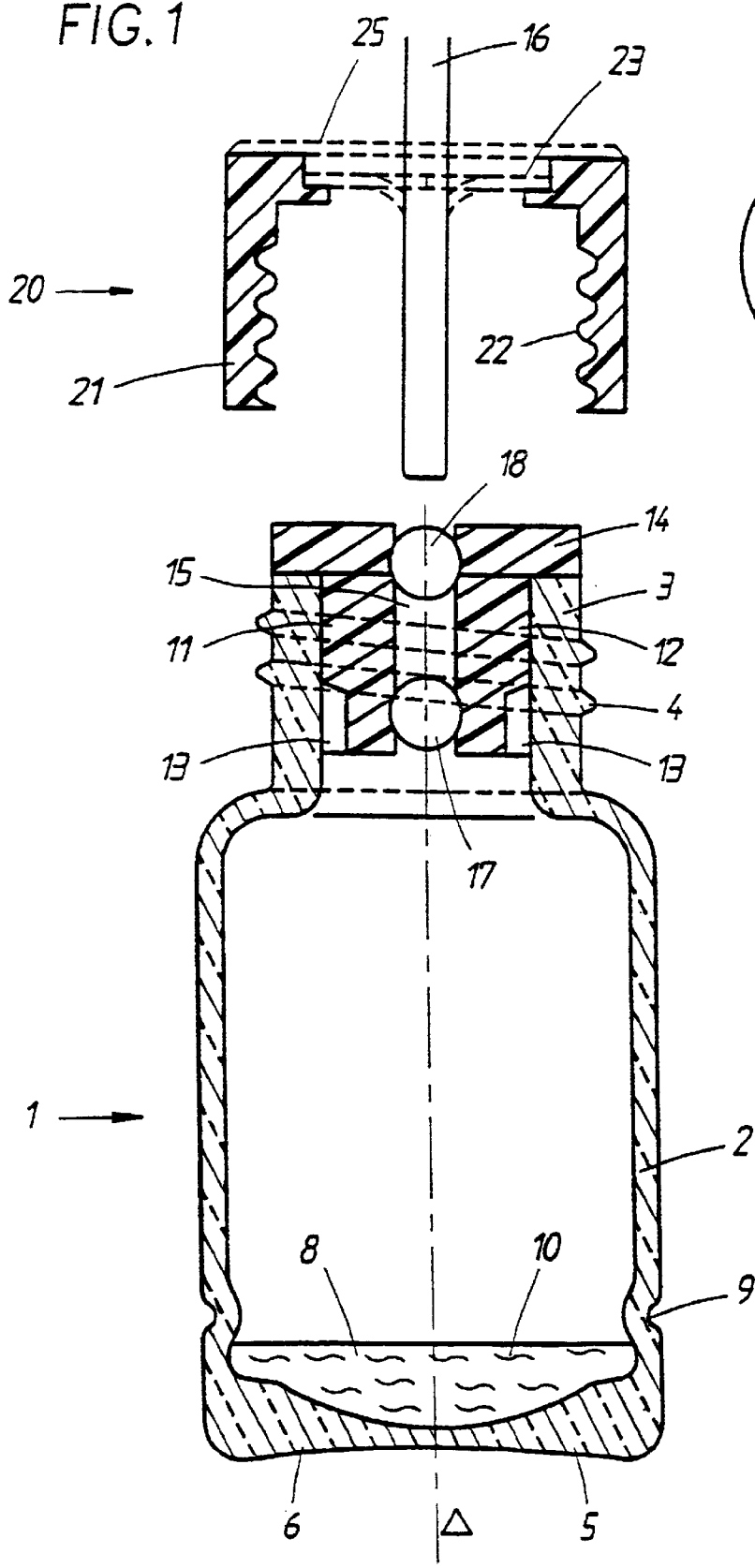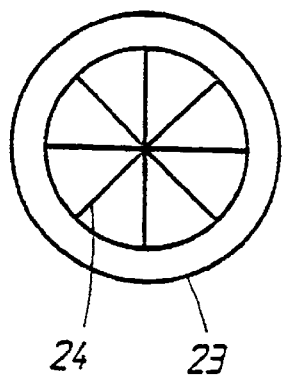

SEAL FOR REAGENT FLASK USABLE BY A BLOOD ANALYZER

FIELD OF THE INVENTION

The present invention concerns a seal for a reagent flask usable by a blood analyser.

It can be applied, in particular but not exclusively, to the packaging of reagents ready for use or even freeze-dried reagents intended to be restored prior to use with a solvent and/or a diluting agent, such as distilled water.

Normally, the flasks used for this type of application are closed off with a stopper or cap made of an elastic material designed to be able to be perforated by and injection and/or suction needle having a generally bezel-cut pointed end.

This needle has been designed so as to move coaxially to the flask and traverse the stopper or cap and then become engaged inside the flask so as to be immobilised in a suction position in which the suction orifice is situated a short way from the bottom. This distance is determined so as to avoid any clogging and/or deterioration of the needle in contact with the bottom.

It is clear that only the reagent volume situated above the upper end of the orifice of the needle could be sucked up, the volume situated below constituting an unused dead volume. It appears that this dead volume, which depends on the shape of the bottom and the obliqueness of the point of the needle, is relatively large.

Of course, operators have tended to reuse this dead volume by pouring it into another flask or receptacle containing a reagent of the same type. However, this practice is to be prohibited owing to the fact that it constitutes a source of a serious error: it compromises the quality, composition and concentration of the reagent.

SUMMARY OF THE INVENTION

The object of the invention is thus to reduce to a strict minimum this dead volume.

To this effect, it thus provides a seal including an elastic stopper able to be engaged sealed inside the neck of the flask and having a coaxial channel for the passage of and injection and/or sampling needle, this channel being sealed by at least one ball having a diameter slightly larger than that of the channel.

Advantageously, said channel could be sealed by two balls respectively engaged at the level of its ends.

This solution, which is particularly suitable when the bottom of the flask has a concave bottom, offers a large number of advantages.

Thus, before restoring and/or using the reagent, the channel is sealed at each of its ends and therefore is unable to contain any material able to then alter the quality of the reagent.

Furthermore, this solution makes it possible to use flat end injection and/or sampling needles (not bevel-cut). Thus, when restoring and/or sampling the reagent, the needle passes through the channel by expelling the two balls which fall into the bottom of the flask. The needle then continues to fall so as to finally stop a short distance from the bottom of the concave form. At the end of this fall, the needle could not be sealed by one of the balls: in fact, the two balls, by resting on the concave bottom, take support on each other and thus moved out of center with respect to the axis of the needle. Therefore, they will thus be separated from each other when the needle moves.

This would not occur if only one ball was available.

During restoring, the balls could advantageously play the role of an agitator so as to dilute the freeze-dried substance.

BRIEF DESCRIPTION OF THE DRAWINGS

There follows hereafter a description of a non-restrictive embodiment example of the invention with reference to the accompanying drawings on which:

FIG. 1 is an axial section of a flask according to the invention and equipped with a stopper and a seal capsule;

FIG. 2 is a top view of a cap equipping the seal capsule;

Figure 3:
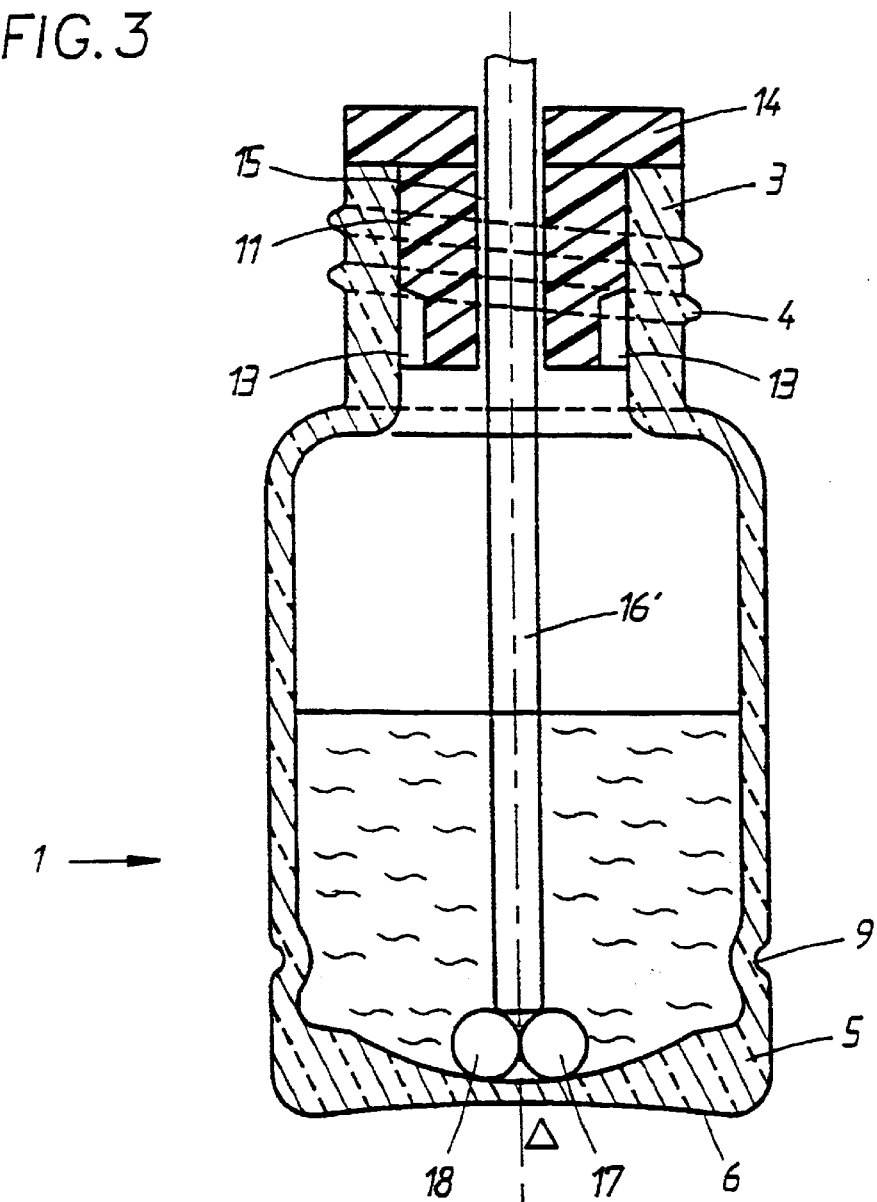
FIG. 3 is an axial section of a flask when engaging a sampling needle.

In this example, the flask 1 has an approximately cylindrical body 2 ended at one of its ends by a neck 3 fitted with external helical threads 4, and, at its other end, by a bottom 5 whose outer wall 6 is relatively flat.

In accordance with the invention, the internal wall 7 of the bottom 5 has an approximately spherical concave shape 8 coaxial to the body 2.

In addition, the cylindrical body 2 includes a re-entering circular ribbing 9 extending parallel to the bottom 6 coaxially and a short distance from the latter.

This ribbing 9 is used to retain the freeze-dried reagent cake 10 before being restored in a blood analyser.

In this example, the flask 1 is sealed by a stopper 11 made of a resilient material, such as rubber or elastomer.

This stopper 11 includes an approximately cylindrical portion 12 whose diameter is slightly larger than the neck 3 and has in its lower portion axial grooves 13 used as vents to allow the vapour to pass when freeze-drying the reagent previously in liquid form inside the flask 1. At its upper end, it comprises a flange 14 whose diameter is almost equal the outer diameter of the neck 3.

This stopper 11 further comprises a traversing coaxial central passage 15 allowing the passage of a flat end injection and/or sample needle 16 (cut perpendicular to its axis). In fact, the use of a bevelled end needle allowing piercing of the stopper 11 would not be suitable. Contrary to the sought-after aim, it would generate a dead reagent volume over almost the entire height of the bevelled portion.

Forcibly engaged inside the passage 15 are two spherical balls 17, 18 whose diameter is slightly larger than that of the passage 15.

These two balls 17, 18, which are respectively disposed close to the upper and lower faces of the stopper 11 ensure double imperviousness at the level of two respective equatorial planes perpendicular to the axis of the passage 15. This disposition ensures that the central volume of the passage cannot be used as a receptacle for the reagent or foreign substances likely to change the nature of the reagent.

Closing of the flask 1 is further completed by using a seal capsule 20 having a cylindrical skirt 21 whose internal wall is fitted with an internal screw thread 22 able to be screwed onto the threads 4 of the neck 3.

This capsule 20 is reclosed at its upper end by a compound-filled cap 23 made of an elastic material, such as rubber or an elastomer. As can be seen on FIG. 2, this cap 23 has the shape of a disk fitted with a plurality of radiant slots 24 each ending at a specific distance from the circular edge of the disk.

As shall be explained hereafter, this cap 23 permits the passage of an injection, and/or sampling needle and then seals off this passage when extracting the needle, thus reducing to a minimum the evaporation phenomena of the reagent.

In the case where the flask 1 contains a freeze-dried cake 10, the first operational phase to be carried out is restoring the reagent. To this effect, an injection needle 16 is introduced in the flask 1 via the passage 15. When being introduced, the needle 16, which traverses the cap 23 progressively expels the balls 17, 18 which, when coming out of the passage 15, fall into the flask 1 on the freeze-dried cake 10 (The balls can be expelled before introducing the needle by any suitable device).

The analyser then injects a predetermined quantity of solvent or diluting agent and by agitating the flask 1 produces a mixture. During agitation, the balls 17, 18 carry out a mechanical action of the freeze-dried substance similar to that of an agitator, and contribute in ensuring perfect homogeneity of the mixture.

Sampling can then be provided by means of a sampling needle 16' (possibly the same as the injection one) whose lower end is brought close the bottom 5. Initially the balls 17, 18 are disposed symmetrically against each other with respect to a plane of symmetry passing through the axis Δ of the flask 1.

Figure 4:
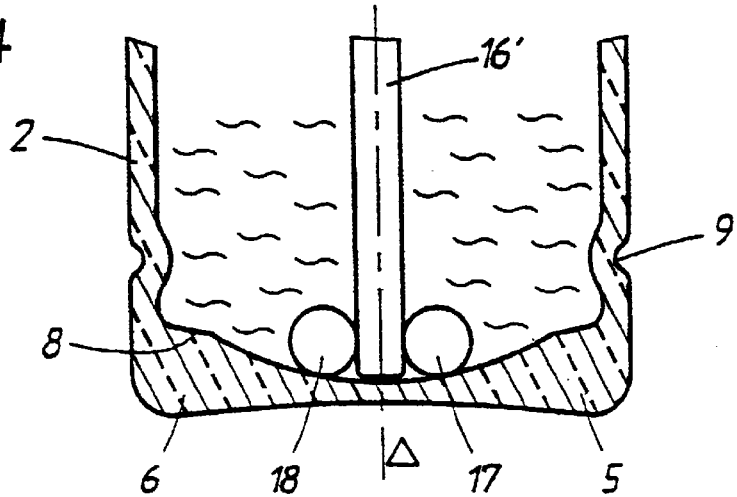
FIG. 4 is a view of the lower portion of the flask showing the end of the needle engaged between the two balls coming from the stopper.

Because of this, the end of the needle 16', whose diameter is smaller than the distance separating the center of the two balls 17, 18, shall play the role of a wedge by being inserted between said balls 17, 18 so as to be able to arrive close to the bottom (FIG. 4). This thus ensures that the end of the needle 16' does not stop on a ball 17, 18 and is unable to therefore approach the bottom 5.

After each sampling phase, the needle 16' can be extracted from the flask 1. In this case, the cap 23, by retaking its initial position, ensures sufficient sealing so as to avoid the reagent evaporating outside the flask.

Of course, the invention is not merely limited to the previously embodiment.

Thus, the passage 15 could be adjusted so as to ensure improved placing of the balls 17, 18. Similarly, a self-adhesive protection cap 25 could be placed on the upper face of the seal capsule 20 or the stopper 11.

What is claimed is:

1. Seal for a reagent flask usable by a blood analyser said blood analyser comprising an injection and/or straight end sampling needle, said flask comprising a tubular body ended on one side by a bottom and on the other side by a neck able to be sealed by a stopper made of an elastic material, said stopper comprising a coaxial central channel used for the passage of an injection and/or sampling needle, said channel being sealed off by at least one ball having a diameter slightly larger than that of the channel, wherein said channel is sealed off by two balls respectively engaged at the level of their ends.

2. Seal according to claim 1, wherein the internal wall of said bottom has a concave shape whose depth gradually increases towards the center of the bottom where it reaches a maximum value.

3. Seal according to claim 2, wherein said concave shape is approximately spherical.

4. Seal according to claim 2, wherein the two balls each have a diameter larger than the outer diameter of the injection and/or sampling needle.

5. Seal according to claim 4, wherein the needle of said blood analyser has an end cut perpendicular to its axis.

6. Seal according to claim 1, wherein said stopper comprises a cylindrical portion having a diameter larger than the internal diameter of the neck, this cylindrical portion having in its lower portion axial grooves used as vents.

7. Seal according to claim 1, wherein it comprises a seal capsule comprising a circular skirt adjusted to be able to be screwed on threads provided on the neck.

8. Seal according to claim 7, wherein the capsule is reclosed at the level of its upper end by a compound-filled cap made of an elastic material and having a plurality of radiant slots meeting at the center and ending at a specific distance from its circular edge.

9. Seal according to claim 7, wherein a self-adhesive protection cap is placed on the upper face of the capsule and/or the stopper.

* * * * *